United States Patent
Van Heerden et al.

(10) Patent No.: US 6,640,118 B2
(45) Date of Patent: Oct. 28, 2003

(54) SQUEEZABLE ELECTRODE ASSEMBLY

(75) Inventors: Clive R. Van Heerden, Bronx, NY (US); George Marmaropoulos, Yorktown Heights, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/084,725

(22) Filed: Feb. 25, 2002

(65) Prior Publication Data

US 2003/0163035 A1 Aug. 28, 2003

(51) Int. Cl.$^7$ .............................. A61B 5/04; A61N 1/04
(52) U.S. Cl. ................. 600/372; 600/397; 607/149; 607/152; 607/153
(58) Field of Search ................. 600/372, 395–397; 601/21; 604/20; 607/149, 152, 153

(56) References Cited

U.S. PATENT DOCUMENTS

| | | | |
|---|---|---|---|
| 4,166,457 A | * | 9/1979 | Jacobsen et al. ............. 600/397 |
| 4,300,575 A | | 11/1981 | Wilson ........................ 128/798 |
| 6,198,955 B1 | | 3/2001 | Axelgaard et al. ........... 600/391 |
| 6,263,226 B1 | | 7/2001 | Axelgaard et al. ........... 600/391 |

* cited by examiner

Primary Examiner—Lee Cohen
(74) Attorney, Agent, or Firm—Aaron Waxler

(57) ABSTRACT

There is provided a skin engageable, electrode assembly for making selectable contact with the skin. The electrode facilitates the selective collection of electrical data and/or provides selective electrical stimulation. The electrode includes a conductive element, preferably of fabric construction, a semi-fluid conductive layer surrounding the conductive element, a cover preferably made of a perforated fabric or other porous material cell, and one or more temperature sensitive wires embedded in the cover that constrict when heated to cause the semi-liquid conductive layer to permeate the cover via the pores to engage the skin for electrical communication. When the wires cool, they loosen causing the semi-fluid conductive layer to be reabsorbed within the cover to prevent electrical communication with the skin.

20 Claims, 1 Drawing Sheet

SQUEEZABLE ELECTRODE ASSEMBLY

FIELD OF THE INVENTION

The present invention relates to an electrode assembly. More particularly, the present invention relates to a skin engageable, conductive silicon electrode assembly adapted for making selectable contact with the skin.

DESCRIPTION OF THE PRIOR ART

The use of conductive silicon electrodes is well known in connection with various medical and bio-sensing applications. These types of electrodes are of particular interest to those developing wearable electronic and sensor devices. The potential and varied applications for these wearable devices has created a need to develop a skin engageable electrode assembly capable of being integrated into an article of clothing for selectively making contact with the skin. This is advantageous as it helps to reduce discomfort and improve efficient electrical communication between the skin and the electrode during use.

SUMMARY OF THE INVENTION

It is an object of the present invention to provide an improved skin engageable, conductive silicon electrode assembly.

It is another object of the present invention to provide such an improved electrode assembly adapted for making selectable contact with the skin.

It is still another object of the present invention to provide such an improved electrode assembly adapted for selectively collecting electrical data and/or providing electrical stimulation.

It is yet another object of the present invention to provide such an improved electrode assembly configured for use with various wearable electronic devices and/or sensors.

It is a further object of the present invention to provide such an improved electrode assembly for use with various electrical instruments, including medical instruments.

It is still a further object of the present invention to provide such an improved electrode assembly for enhancing comfort and efficiency (does not require extensive preparatory steps by a user) for long-term wear.

These and other objects and advantages of the present invention are achieved by an electrode assembly that includes a conductive element, a semi-fluid conductive layer surrounding the conductive element, a cover having an inner surface and adapted to surround the conductive element and the semi-fluid conductive layer, and a plurality of temperature sensitive wires embedded in the inner surface of the cover. Preferably, the conductive element has a fabric construction. Preferably, the semi-fluid conductive layer is a layer of silicon gel. And preferably, the cover is made of a perforated fabric or other similar material cell.

BRIEF DESCRIPTION OF THE DRAWINGS

The present invention is more fully understood by reference to the following detailed description of a preferred embodiment in combination with the drawings identified below.

DETAILED DESCRIPTION OF THE INVENTION

Figure 1:
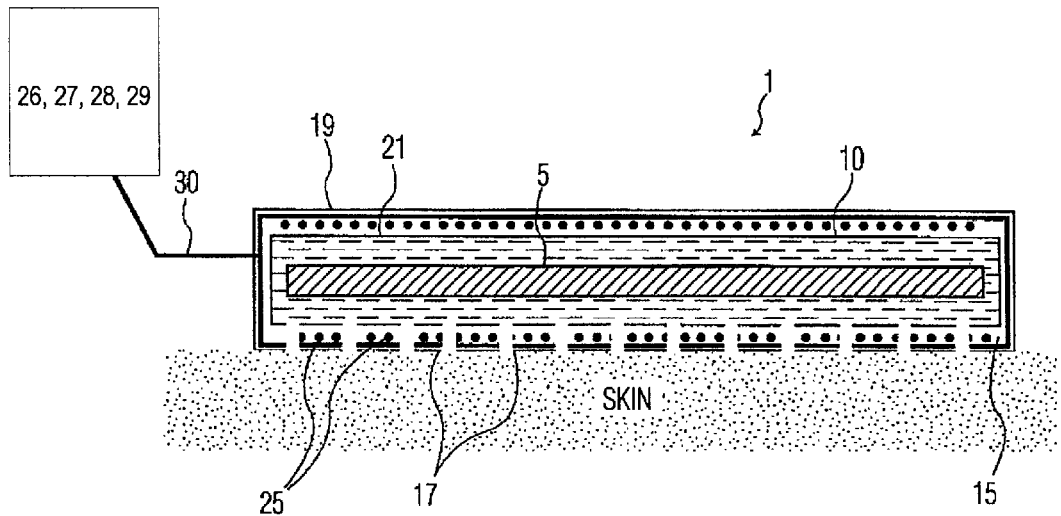
FIG. 1 is a cross-section side view of an improved electrode assembly in accordance with a preferred embodiment of the present invention, showing the electrode in a relaxed stage.
Figure 2:
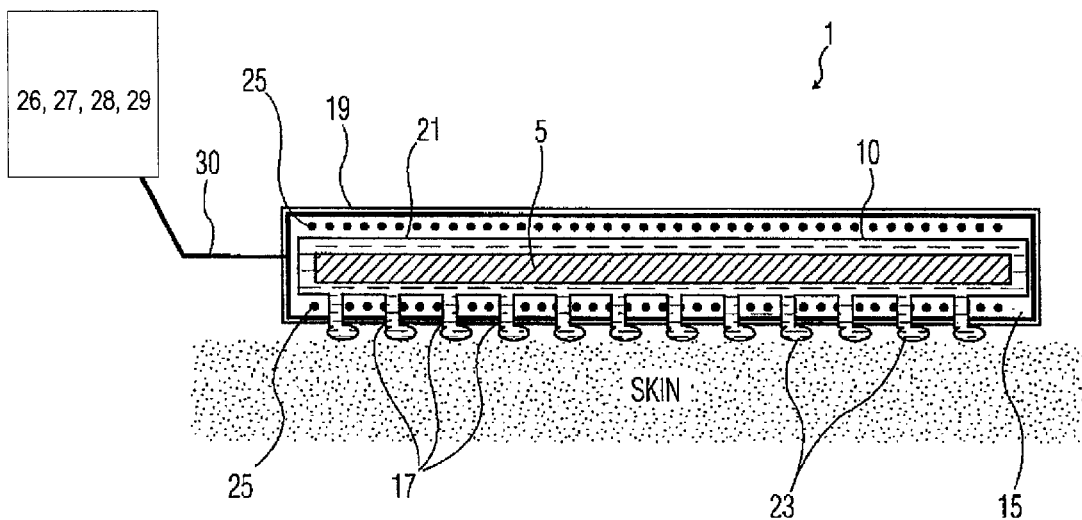
FIG. 2 is a second cross-section side view of the electrode assembly of FIG. 1, showing the electrode in a constricted stage.

Referring to FIGS. 1 and 2, there is shown an improved electrode assembly in accordance with a preferred embodiment of the present invention generally represented by reference numeral 1. The electrode assembly 1 has a conductive element 5, a semi-fluid conductive layer 10 surrounding conductive element 5, a cover 15 surrounding the conductive element and the semi-fluid conductive layer, and one or more conductive elements or temperature sensitive wires 25 embedded or incorporated in cover 15.

Conductive element 5 preferably has a tightly woven fabric construction. However, different weave patterns may be used to facilitate different applications in use. Preferably, the fabric construction is made from a conductive material, including, for example, metalized foils, conductive polymers, graphitized or metalized cloth or wire mesh. Conductive element 5 is preferably also connected to an electrical power source 26, an electrical instrument 27, a wearable electronic device 28 or a wearable electronic sensor 29 via a connector 30. Preferably, connector 30 provides a medium for electrical communication between conductive element 5 and the electrical power source. Connector 30 may be fashioned in any suitable manner to facilitate electrical communication. For example, connector 30 can be a lead wire running between conductive element 5 and the electrical power source. Conductive element 5 can preferably also have different shapes or sizes. Thus, conductive element 5 can be shaped and sized for different uses.

Semi-fluid conductive layer 10 is preferably made of an electrically conductive silicon gel. However, any material having a similar conductivity and viscosity to that of silicon gel may also be used. Conductive layer 10 preferably facilitates the selective electrical communication between conductive element 5 and the skin.

Cover 15 is preferably made of a woven fabric having a plurality of pores 17, such as for example, a mock leno fabric, an airtex, or another material cell. Preferably, cover 15 has a double-faced fabric with a first outer face 19 and a second inner face 21. First outer face 19 is preferably made of a conductive yarn, as for example, a silver conductive yarn. Other materials having sufficient porosity and conductivity to facilitate selective electrical communication between conductive layer 10 and the skin may also be used. Second inner face 21 is preferably made of a material having a warp of polyester and at least two wefts. However, it is clear that other types and patterns of material may also be used. Second inner face 21 is preferably connected to semi-fluid conductive layer 10 by sonic welding. However, other connecting methods may also be used. Preferably, cover 15 is produced by first, weaving the double faced fabric, and second, cutting the fabric in an amount sufficient to adequately and securely enclose conductive element 5 and semi-fluid conductive layer 10.

Each wire 25 is preferably made of a temperature sensitive memory alloy, such that when the wire is heated, by an electric current, the wire squeezes or constricts assembly 1. This squeezing or constricting action causes semi-fluid conductive layer 10 to permeate cover 15 through pores 17, thereby creating one or more electrical contacts 23. The electrical contacts 23 preferably touch the skin to create an electrical communication between the electrical power source, conductive member 5 and the skin. Preferably, when wires 25 cool in the absence of electric current, the wires return to their original shape and configuration, thereby causing the re-absorption, via pores 17, of semi-fluid conductive layer 10. Accordingly, conductive layer 10 is once again enclosed in cover 15 causing the electrical contacts 23 to be terminated.

Thus, wires 25, preferably, enable the selective electrical communication between the electronic power source and the skin. This electrical communication preferably facilitates performing various operations. For example, such operations include providing selective electronic massage therapy, selectively collecting and recording electronic data, and/or providing selective electrical stimulation.

Electrode assembly 1 can preferably be used in conjunction with a variety of electrical mechanisms. For example, such mechanisms include a wearable device or sensor, a medical instrument, and different health and fitness therapy devices. Electrode assembly 1 can preferably be any desired shape, size or configuration necessary to perform the desired function. Thus, electrode assembly 1 is preferably a highly flexible and lightweight high-performance electrode that is capable of making selective contact with the skin to improve comfortability and enable long-term wear.

The present invention having been thus described with particular reference to the preferred forms thereof, it will be obvious that various changes and modifications may be made therein without departing from the spirit and scope of the present invention as defined herein.

What is claimed is:

1. An electrode assembly comprising:
   a first conductive element;
   a semi-fluid conductive layer about said first conductive element;
   a porous cover about said conductive layer and said first conductive element; and
   one or more second conductive elements for cooperating with said porous cover to affect said semi-fluid conductive layer.

2. The electrode assembly of claim 1, wherein said first conductive element has a fabric construction.

3. The electrode assembly of claim 1, wherein said semi-fluid conductive layer has a viscosity to enable selective permeation through said cover.

4. The electrode assembly of claim 1, wherein said semi-fluid conductive layer is made of silicon gel.

5. The electrode assembly of claim 1, wherein said cover is made of a material with a resilient porous construction.

6. The electrode assembly of claim 1, wherein said porous cover allows said semi-fluid conductive layer to selectively permeate therethrough.

7. The electrode assembly of claim 1, wherein said one or more second conductive elements are wires.

8. The electrode assembly of claim 7, wherein said wires are temperature sensitive wires.

9. The electrode assembly of claim 8, wherein said temperature sensitive wires constrict when heated by electric current.

10. The electrode assembly of claim 9, wherein said temperature sensitive wires loosen and return to their original shape when cooled.

11. The electrode assembly of claim 8, wherein said temperature sensitive wires are made of a memory alloy.

12. The electrode assembly of claim 1, wherein said first conductive element has a connector that is connectable to an electrical power source.

13. The electrode assembly of claim 1, wherein said first conductive element has a connector that is connectable to an electrical instrument.

14. The electrode assembly of claim 1, wherein said first conductive element has a connector that is connectable to a wearable electronic device.

15. The electrode assembly of claim 1, wherein said first conductive element has a connector that is connectable to a wearable electronic sensor.

16. An electrode assembly comprising;
   a first conductive element;
   a semi-fluid conductive layer enclosing said first conductive element;
   a perforated cover having a plurality of pores, said cover enclosing said conductive layer and said first conductive element; and
   one or more temperature sensitive wires embedded in said perforated cover and adapted to constrict when heated by electric current and loosen when cooled.

17. A method for making selective electrical contact with the skin, comprising the steps of:
   providing an electrode assembly having at least one first conductive element, at least one semi-fluid conductive layer enclosing said at least one first conductive element, at least one porous cover, said cover enclosing said conductive layer and said first conductive element, and one or more memory wires for cooperating with said porous cover and said at least one semi-fluid conductive layer; and
   selectively heating said one or more memory wires thereby causing said at least one porous cover to constrict about said at least one semi-fluid conductive layer in turn causing said at least one semi-fluid layer to permeate said porous cover to form one or more skin engaging electrical contact areas.

18. The method of claim 17, further comprising the step of selectively cooling said one or more memory wires thereby causing said at least one porous cover to loosen about said at least one semi-fluid conductive layer in turn causing said at least one semi-fluid conductive layer to be reabsorbed by said porous cover to prevent said formation of said one or more skin engaging electrical contact areas.

19. The method of claim 18, wherein said one or more skin engaging electrical contact areas can make either continuous or selectable contact with the skin.

20. The method of claim 19, further comprising the step of connecting said at least one first conductive element with an electronic device.

* * * * *